US00PP29134P2

(12) United States Plant Patent
Van Swieten

(10) Patent No.: US PP29,134 P2
(45) Date of Patent: Mar. 20, 2018

(54) *PHALAENOPSIS* ORCHID PLANT NAMED 'PHALFOXYQ'

(50) Latin Name: ***Phalaenopsis* hybrid**
Varietal Denomination: Phalfoxyq

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/530,425

(22) Filed: Jan. 12, 2017

(51) Int. Cl.
*A01H 5/02* (2006.01)

(52) U.S. Cl.
USPC ..... Plt./311

(58) Field of Classification Search
USPC ..... Plt./311
See application file for complete search history.

(56) References Cited

PUBLICATIONS

PLUTO Plant Variety Datbase Dec. 8, 2017 p. 1.*

* cited by examiner

*Primary Examiner* — Annette H Para
(74) *Attorney, Agent, or Firm* — Jondle & Associates, P.C.

(57) ABSTRACT

A new and distinct variety of *Phalaenopsis* plant named 'PHALFOXYQ', particularly characterized by having dark purple-red flowers with a light purple center and edge and a purple lip, 1 to 3 peduncles that are long and sturdy, leaves that are oblong, and is propagated by meristem tissue culture, is disclosed.

3 Drawing Sheets

Genus and species: *Phalaenopsis* hybrid.
Variety denomination: 'PHALFOXYQ'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFOXYQ'.

The new *Phalaenopsis* plant is a product of a planned breeding program conducted by the inventor in Bleiswijk, The Netherlands. The objective of this breeding program was to create a new *Phalaenopsis* plant with numerous attractive and unique dark purple-red flowers with a light purple center and edge and a purple lip, suitable for potted plant production.

The new *Phalaenopsis* plant 'PHALFOXYQ' is a result of cross-pollination made by the inventor in February 2007 in Bleiswijk, The Netherlands of the proprietary female, or seed parent, *Phalaenopsis* hybrid '01-1941' (unpatented) with the proprietary male, or pollen parent, *Phalaenopsis* hybrid '23426-04' (unpatented).

The new *Phalaenopsis* was selected by the inventor as a single plant within the progeny of the stated cross-pollination in a controlled greenhouse in Bleiswijk, The Netherlands in February 2010. Asexual reproduction of the new *Phalaenopsis* plant by meristem tissue culture since 2012 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 18, 2016. 'PHALFOXYQ' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALFOXYQ' as a new and distinct variety of *Phalaenopsis* plant.

1) Dark purple-red flowers with a light purple center and edge and a purple lip;
2) 1 to 3 peduncles;
3) Peduncle is long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, The Netherlands, from 50-week old plants in November 2016. Colors in the photographs may differ from the color values cited in the detailed botanical description, which accurately describe the actual colors of the new variety.

DESCRIPTION OF THE NEW VARIETY

Figure 1:
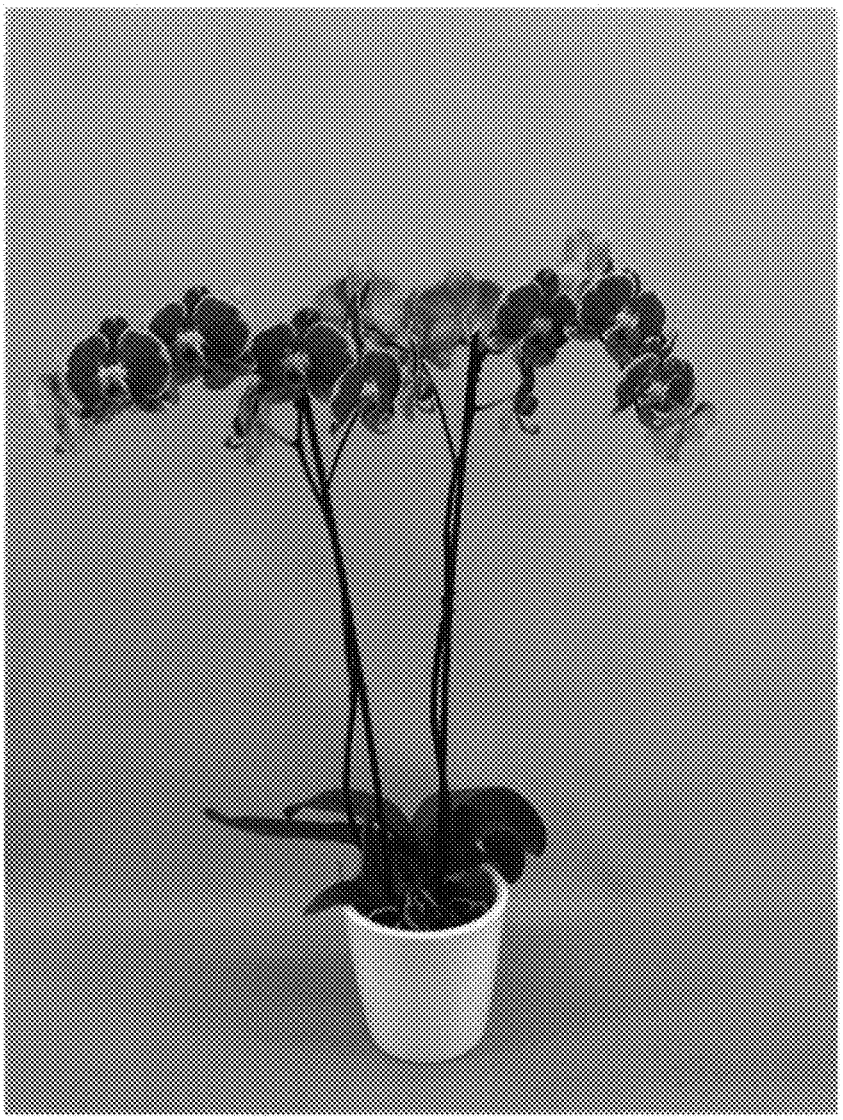
FIG. 1 shows the overall plant habit, including blooms and foliage of 'PHALFOXYQ'.
Figure 2:
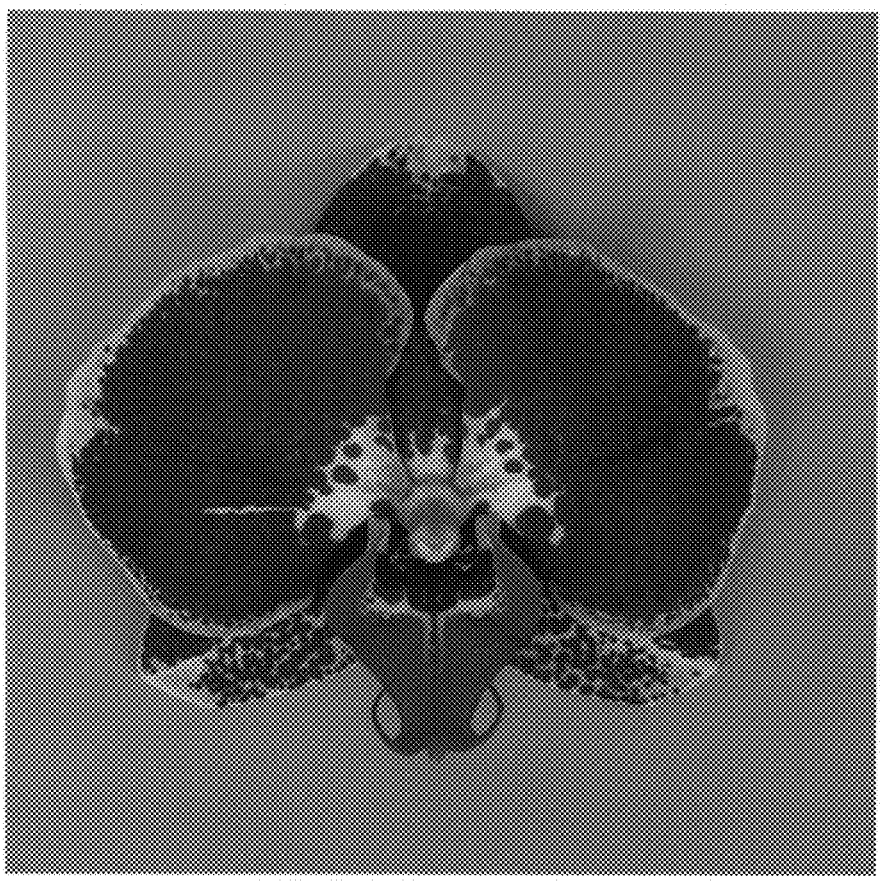
FIG. 2 shows a close-up of a flower of 'PHALFOXYQ'.
Figure 3:
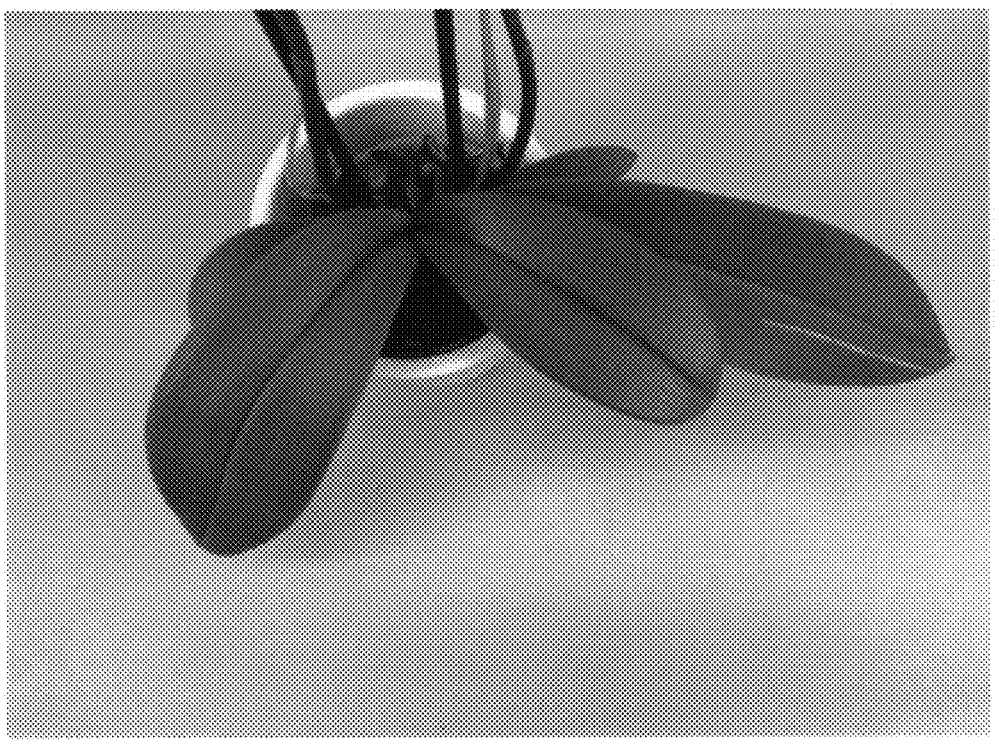
FIG. 3 shows a close-up of the leaves of 'PHALFOXYQ'.

The following detailed description sets forth the distinctive characteristics of 'PHALFOXYQ'. Plants of the new

*Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in November 2016 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALFOXYQ'.

Parentage:

*Female parent*.—*Phalaenopsis* cultivar '01-1941' (unpatented).

*Male parent*.—*Phalaenopsis* cultivar '23426-04' (unpatented).

Propagation:

*Type*.—Meristem tissue culture.

Roots:

*Root description*.—Greyed-green (RHS 193A) colored roots with light branching lateral roots having red-purple (RHS 183D) colored root tips.

Plant:

*Commercial crop time to flowering*.—Approximately 48 to 50 weeks from a rooted cutting to finish in a 12 cm pot.

*Growth habit of peduncle*.—Standard, green leaves, raceme to panicle.

*Height* (*from soil level to top of inflorescence*).—Approximately 49.0 cm to 59.0 cm.

*Width* (*measured from leaf tips*).—About 28.0 cm to 33.0 cm.

*Vigor*.—Moderate.

Leaves:

*Mature leaves*.—Quantity per plant: 6 to 8 leaves are produced before flowering. Length (fully expanded): 15.0 cm to 17.0 cm. Width: 7.0 cm to 8.0 cm. Shape: Oblong. Base shape: Moderately elongated. Apex: Unequal obtuse. Leaf blade angle with the petiole (measured from the horizontal position): Between 20 degrees and 35 degrees. Leaf margin: Entire. Color: Upper surface: RHS 146A. Lower surface: RHS 146B with slightly dark red edge (RHS 187A). Texture: Slightly rough. Thickness: 2.2 mm to 2.4 mm. Venation: Pattern: Parallel. Color of the midvein: Upper surface: RHS 146A. Lower surface: RHS 146B.

Peduncle:

*Quantity per plant*.—1 to 3.

*Number of flowers per peduncle*.—8 to 14.

*Length*.—50.0 cm to 60.0 cm.

*Diameter*.—4.6 mm to 4.8 mm.

*Strength*.—Moderate.

*Aspect*.—Upright to slightly pendant.

*Texture*.—Smooth.

*Color*.—Brown (RHS 200A) with a touch of greyed-green (RHS 195A).

*Internode length*.—40.0 mm to 50.0 mm.

*Callosities*.—None.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 160.0 mm to 180.0 mm.

*Flowering time*.—First flowers can be expected 10 to 11 months after planting in a 12 cm (diameter) pot.

*Flower*.—Height: 73.0 mm to 75.0 mm. Diameter: 85.0 mm to 90.0 mm. Depth of lip: 22.0 mm to 24.0 mm.

*Flower longevity*.—On the plant: 15 to 19 weeks.

*Fragrance*.—Absent.

*Flower bud*.—Average size: Medium to large. Length: 22.0 mm to 24.0 mm. Width: 19.0 mm to 21.0 mm. Shape: Egg shaped. Color: Purple-red (RHS N79B) and green (RHS 146D).

*Petals*.—Arrangement: Open/free. Shape: Semi-circular. Apex: Slightly emarginated asymmetric. Margin: Undulated. Length (from base to tip): 40.0 mm to 42.0 mm. Width: 51.0 mm to 53.0 mm. Color (when fully opened): Upper surface: Basic color: Dark purple-red (RHS N79C). Over color: Light purple edge and center (RHS N80D). Lower surface: Basic color: Light purple (RHS 76B). Over color: Purple (RHS N78D).

*Dorsal sepal*.—Shape: Elliptic. Apex: Emarginated symmetric. Margin: Entire. Length (from base to tip): 41.0 mm to 43.0 mm. Width: 30.0 mm to 32.0 mm. Color (when fully opened): Upper surface: Basic color: Dark purple-red (RHS N79C). Over color: Light purple (RHS N80D). Lower surface: Basic color: Light purple (RHS 76A/B). Over color: Purple (RHS N78D).

*Lateral sepals*.—Shape: Ovate. Apex: Obtuse asymmetric. Margin: Entire. Length (from base to tip): 42.0 mm to 44.0 mm. Width: 26.0 mm to 28.0 mm. Color (when fully opened): Upper surface: Basic color: Dark purple-red (RHS N79C). Over color: Light purple (RHS 76B and N78C). Lower surface: Basic color: Light purple (RHS 76B). Over color: Purple (RHS N78B) towards the apex.

*Labellum* (*lip*).—Whiskers: Present. Length of whiskers: 17.0 mm to 19.0 mm. Color of whiskers: Purple (RHS N78A) with slightly dotted tips. Pubescence on the lip: Absent.

*Lateral lobe*.—Shape: Spatulate. Margin: Undulated. Length: 19.0 mm to 21.0 mm. Width: 14.0 mm to 16.0 mm. Color: White (RHS N155C) with a red-purple (RHS 59A/B) fleck at the base and purple (RHS NN78A) edge.

*Apical lobe*.—Shape: Triangular. Margin: Entire. Length: 17.0 mm to 19.0 mm. Width: 20.0 mm to 22.0 mm. Color: Red-purple (RHS 59A/B) at the base with slightly dotted (RHS 59A/B) wings; purple (RHS NN78A/B) towards the whiskers.

*Callus*.—Average size: Medium. Height: 0.6 cm to 0.7 cm. Length: 0.6 cm to 0.7 cm. Width: 0.4 cm to 0.5 cm. Color: Dark red (RHS 187A), slightly yellow (RHS 4A) on the side.

*Reproductive organs*.—Column: Length: 7.0 mm to 9.0 mm. Diameter: 5.4 mm to 5.7 mm. Color: Purple (RHS N78B). Pollinia: Quantity: 2. Diameter: 0.9 mm to 1.1 mm. Color: Orange (RHS 25A). Ovary: Length: 8.0 mm to 10.0 mm. Diameter: 2.3 mm to 2.6 mm. Pedicel: Length: 36.0 mm to 38.0 mm. Diameter: 3.0 mm to 3.3 mm. Color: Green (RHS 146B and 145C) at the base; light purple (RHS 76B) towards the flower.

Disease, pest, and stress resistance: Resistance to pathogens and pests common to *Phalaenopsis* has not been observed.

Fruit and seeds: Fruit and seed development has not been observed on plants of the new *Phalaenopsis*.

COMPARISON WITH PARENTAL AND SIMILAR COMMERCIAL VARIETIES

'PHALFOXYQ' differs from female parent '01-1941' (unpatented) in that 'PHALFOXYQ' has dark purple-red flowers with a center and edge pattern, whereas cultivar '01-1941' has white flowers with a spotted pattern and striped edge.

'PHALFOXYQ' differs from male parent '23426-04' (unpatented) in that 'PHALFOXYQ' has dark purple-red (RHS N79C) flowers with a center and edge pattern, whereas '23426-04' has purple (RHS N78B) flowers with an even pattern.

'PHALFOXYQ' is most similar to the commercial *Phalaenopsis* plants named 'PHALFENCK' (unpatented) and 'PHALDISAM' (U.S. Plant Pat. No. 27,203). 'PHALFOXYQ' differs from the commercial variety 'PHALFENCK' in that 'PHALFOXYQ' has dark purple-red flowers with a center and edge pattern and an emarginated dorsal sepal apex, whereas 'PHALFENCK' has red-purple flowers with an edge pattern and a rounded dorsal sepal apex. Additionally, 'PHALFOXYQ' has longer whiskers than 'PHALFENCK'.

'PHALFOXYQ' differs from the commercial variety 'PHALDISAM' in that 'PHALFOXYQ' has dark purple-red flowers with a center and edge pattern and an emarginated dorsal sepal apex, whereas 'PHALDISAM' has white flowers with a flecked pattern and an obtuse dorsal sepal apex. Additionally, 'PHALFOXYQ' has much longer whiskers than 'PHALDISAM'.

I claim:

1. A new and distinct variety of *Phalaenopsis* plant named 'PHALFOXYQ', substantially as described and illustrated herein.

* * * * *